United States Patent
Ito et al.

(10) Patent No.: US 10,117,573 B2
(45) Date of Patent: Nov. 6, 2018

(54) FUNDUS PHOTOGRAPHY DEVICE

(71) Applicant: NIDEK CO., LTD., Gamagori, Aichi (JP)

(72) Inventors: Koichi Ito, Toyohashi (JP); Naoto Honda, Okazaki (JP)

(73) Assignee: NIDEK CO., LTD., Gamagori (JP)

( * ) Notice: Subject to any disclaimer, the term of this patent is extended or adjusted under 35 U.S.C. 154(b) by 0 days.

(21) Appl. No.: 15/644,073

(22) Filed: Jul. 7, 2017

(65) Prior Publication Data

US 2017/0303782 A1    Oct. 26, 2017

Related U.S. Application Data

(62) Division of application No. 14/671,446, filed on Mar. 27, 2015, now Pat. No. 9,723,978.

(30) Foreign Application Priority Data

Mar. 31, 2014 (JP) .................. 2014-074595
Mar. 31, 2014 (JP) .................. 2014-074596

(51) Int. Cl.
*A61B 3/10* (2006.01)
*A61B 3/12* (2006.01)
*A61B 3/14* (2006.01)

(52) U.S. Cl.
CPC ............ *A61B 3/102* (2013.01); *A61B 3/12* (2013.01); *A61B 3/14* (2013.01)

(58) Field of Classification Search
CPC .............. A61B 3/102; A61B 3/12; A61B 3/14
See application file for complete search history.

(56) References Cited

U.S. PATENT DOCUMENTS 5,214,454 A    5/1993  Sano
5,463,430 A   10/1995  Isogai et al.
(Continued)

FOREIGN PATENT DOCUMENTS

DE    102011053880 A1    3/2013
EP        2 845 534 A1    3/2015
(Continued)

OTHER PUBLICATIONS

Jul. 31, 2015 Partial Search Report issued in European Patent Application No. 15161602.6.
(Continued)

*Primary Examiner* — Jack Dinh
(74) *Attorney, Agent, or Firm* — Oliff PLC

(57) ABSTRACT

A fundus photography device includes: a fundus illumination optical system that illuminates a fundus of an eye by illumination light; a fundus photography optical system; an OCT optical system; an anterior chamber observation optical system for observing an anterior chamber observation image of the eye illuminated by the anterior chamber illumination light source; a first wavelength separation member that sets a first optical axis commonly shared by the fundus illumination optical system and the fundus photography optical system to be coaxial with a second optical axis commonly shared by the OCT optical system and an anterior chamber observation optical system; and a second wavelength separation member that forms the second optical axis by setting an optical axis of the OCT optical system to be coaxial with an optical axis of the anterior chamber observation optical system.

4 Claims, 7 Drawing Sheets

(56) References Cited

U.S. PATENT DOCUMENTS

| | | |
|---|---|---|
| 5,777,340 A | 7/1998 | Ueno |
| 2003/0068164 A1 | 4/2003 | Nanjyo |
| 2007/0159595 A1 | 7/2007 | Fukuma et al. |
| 2007/0222945 A1 | 9/2007 | Tsukada et al. |
| 2013/0195336 A1 | 8/2013 | Uchida |
| 2014/0063451 A1 | 3/2014 | Ono et al. |
| 2014/0232987 A1 | 8/2014 | Westphal et al. |
| 2015/0010226 A1 | 1/2015 | Kubota et al. |

FOREIGN PATENT DOCUMENTS

| | | |
|---|---|---|
| JP | H06-046999 | 2/1994 |
| JP | H08-266479 A | 10/1996 |
| JP | 2001-258850 A | 9/2001 |
| JP | 2005-160549 A | 6/2005 |
| JP | 2007-181631 A | 7/2007 |
| JP | 4869757 B2 | 2/2012 |
| JP | 2012-056292 A | 3/2012 |
| JP | 2013-056274 A | 3/2013 |
| JP | 2013-099646 A | 5/2013 |
| JP | 2013-248376 A | 12/2013 |
| JP | 2014-045901 A | 3/2014 |
| WO | 2013/128680 A1 | 9/2013 |

OTHER PUBLICATIONS

Nov. 7, 2017 Office Action issued in Japanese Patent Application No. 2014-074595.
Nov. 7, 2017 Office Action issued in Japanese Patent Application No. 2014-074596.
May 8, 2018 Office Action issued in Japanese Patent Application No. 2014-074595.

FIG. 7A
FIG. 7B
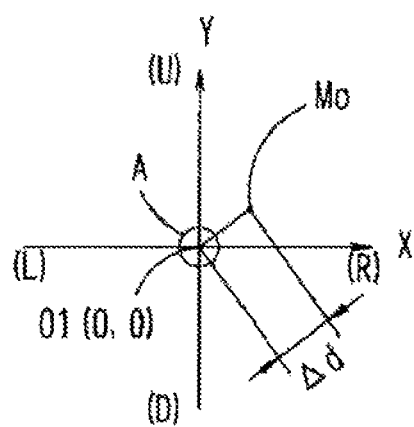
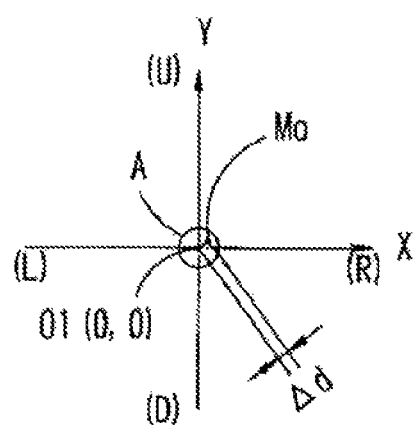

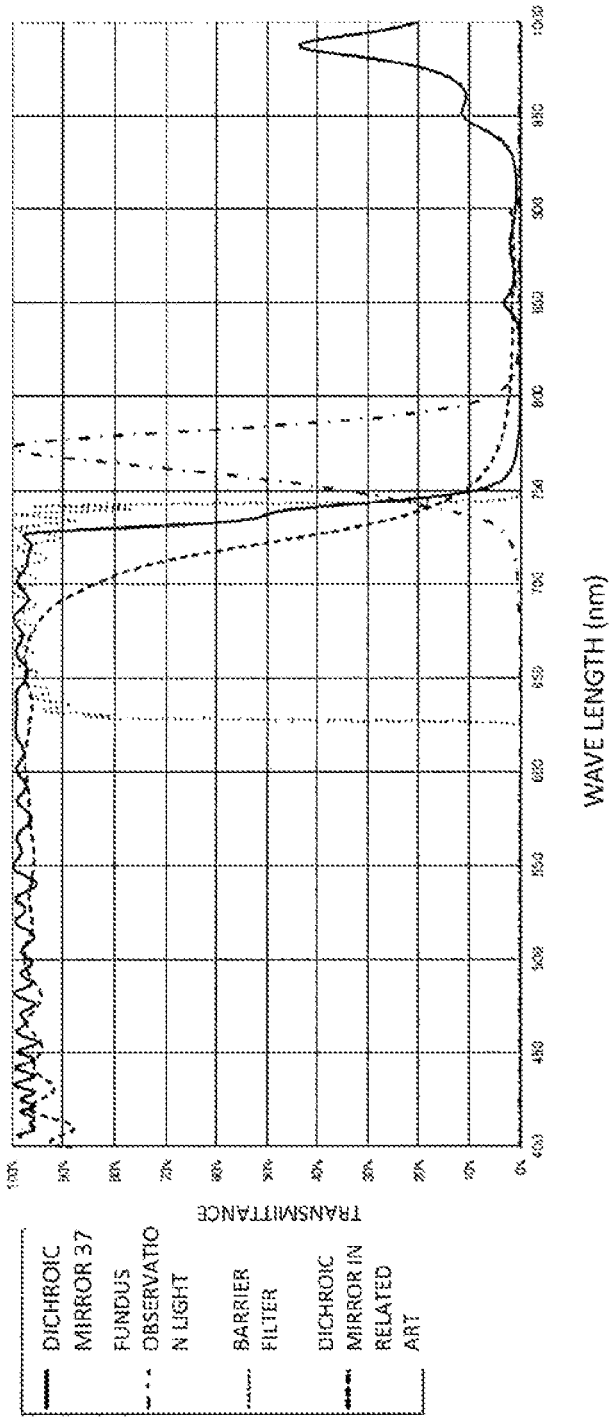

FUNDUS PHOTOGRAPHY DEVICE

CROSS REFERENCE TO RELATED APPLICATIONS

This is a Continuation of application Ser. No. 14/671,446 filed Mar. 27, 2015, which claims the benefit of priorities of Japanese Patent Application No. 2014-074595 filed on Mar. 31, 2014, Japanese Patent Application No. 2014-074596 filed on Mar. 31, 2014 and Japanese Patent Application No. 2013-227562 filed on Oct. 31, 2013, the contents of which are incorporated herein by reference in its entirety.

BACKGROUND

The present invention relates to a fundus photography device that photographs the fundus of a subject's eye.

In the related art, there is known an optical coherence tomography (OCT) using low-coherent light as an ophthalmic device that can non-invasively photograph a tomographic image of a subject's eye.

A complex apparatus including the OCT and a fundus photography device is known (refers to JP-A-2013-056274, and JP-A-2007-181631). In an apparatus disclosed in Patent Document 2, light having a wavelength in the range between 800 nm and 900 nm is used as a signal light from the OCT unit, light having a wavelength in the range between 400 nm and 700 nm is used as an observation light, and light having a wavelength in the range between 700 nm and 800 nm is used as a photography light.

A dichroic mirror is disposed on an optical path of a photography system disclosed in JP-A-2007-181631. The dichroic mirror allows the illumination light (visible light of about 400 nm to 700 nm output from an observation light source) having a wavelength in a visible range emitted from an illumination optical system to pass and reflects the illumination light (near-infrared light of 700 nm to 800 nm output from the photography system) having a wavelength in the near-infrared range.

In the case that the dichroic mirror is used, it is difficult to observe or photograph the fundus image using both the short wavelength light ($\lambda=700$ nm or shorter) and the long wavelength light ($\lambda=700$ nm or longer). As a result, when photographing a fluorescence image of the fundus, the acquired information from the photographed image may be not enough.

SUMMARY

In view of the above problem, an object of an aspect of the present disclosure is to provide a fundus photography device capable of acquiring a good fluorescence fundus image for the complex apparatus including the OCT and the fundus photography device.

The present invention has the following configuration so as to achieve the object.

A fundus photography device comprising:
a fundus illumination optical system including at least a photography light source and an observation light source, the fundus illumination optical system configured to illuminate a fundus of a subject's eye;
a fundus photography optical system including at least a first imaging sensor configured to photograph the fundus, and a second imaging sensor configured to observe the fundus, the fundus photography optical system configured to photograph a front image of the fundus;
an OCT optical system including at least a measuring light path, a reference light path, and a photodetector configured to detect an interference signal between light from the measuring light path and light from the reference path, and configured to obtain a tomographic image of the fundus using optical coherence tomography;
a wavelength selective splitter disposed in an optical path of the fundus photography optical system, and configured to guide a light having a wavelength less than 700 nm and shorter than reflected light of the fundus produced by the observation light source to the first imaging sensor, and configured to guide the reflected light of the fundus produced by the observation light source having a wavelength greater than 700 nm to the second imaging sensor; and
a barrier filter disposed insertably and removably on the optical path of the fundus photography optical system, the barrier filter configured to transmit fluorescent light from the fundus excited by fluorescence excitation light produced by the photography light source, the barrier filter configured to cut off light having wavelengths other than the fluorescent light having a wavelength less than 700 nm.

A fundus photography device comprising:
a fundus illumination optical system including at least a photography light source and an observation light source, the fundus illumination optical system configured to illuminate a fundus of a subject's eye;
a fundus photography optical system including at least a first imaging sensor configured to photograph the fundus, and a second imaging sensor configured to observe the fundus, the fundus photography optical system configured to photograph a front image of the fundus;
an OCT optical system including at least a measuring light path, a reference light path, and a photodetector configured to detect an interference signal between light from the measuring light path and light from the reference path, and configured to obtain a tomographic image of the fundus using optical coherence tomography;
an objective lens configured to be disposed in front of the subject's eye;
a hole mirror;
an anterior eye observation optical system configured to observe an anterior eye of the subject's eye;
a first wavelength selective splitter disposed between the objective lens and the hole mirror, and configured to set a first optical axis commonly shared by the fundus illumination optical system and the fundus photography optical system to be coaxial with a second optical axis commonly shared by the OCT optical system and the anterior eye observation optical system; and
a second wavelength selective splitter disposed upstream of the second wavelength selective splitter, and configured to set an optical axis of the OCT optical system to be coaxial with an optical axis of the anterior chamber observation optical system to form the second optical axis.

BRIEF DESCRIPTION OF THE DRAWINGS

FIGS. 7A and 7B show graphs illustrating the detection of alignment with respect to a subject's eye.

FIG. 8 is a graph illustrating an example of the wavelength characteristics of the optical system of the fundus photography device according to the embodiment.

DESCRIPTION OF ILLUSTRATIVE EMBODIMENTS

Figure 1A:
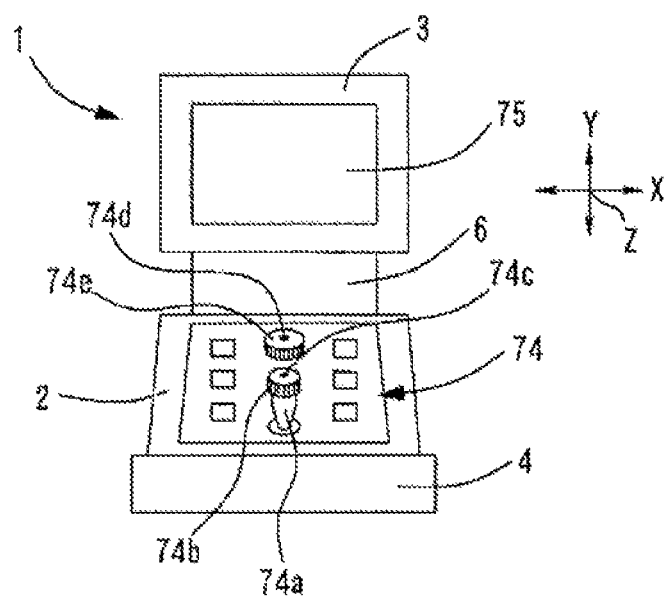
FIGS. 1A and 1B show schematic views illustrating the exterior of a fundus photography device according to an embodiment.

A typical embodiment of the present invention will be described with reference to the accompanying drawings. In the following description of the embodiment, a Z direction (a direction of an optical axis L1) refers to a direction of the depth of a subject's eye, an X direction refers to a horizontal component on a plane (a plane being flush with a subject's face) perpendicular to the direction of the depth, and a Y direction refers to a vertical component on the plane.
<Optical System>

A device 1 mainly includes an objective lens 25; a hole mirror 22; a fundus illumination optical system (hereinafter, an illumination optical system) 10; a fundus photography optical system (hereinafter, a photography optical system) 30; and a coherence optical system (an OCT optical system) 200 (refer to FIG. 2).

For example, the objective lens 25 may be disposed in front of the subject's eye. For example, the hole mirror 22 may include an opening 22a and a mirror portion 22b. The opening 22a may be formed at the center of the mirror portion 22b, and may be disposed eccentrically from the center. The opening 22a may be formed as an actual aperture, may be formed of a glass plate having optical transparency, or may be configured to have the wavelength-selective characteristics by which fundus-reflected light produced by illumination light of the fundus illumination optical system 10 is allowed to transmit therethrough.

For example, the illumination optical system 10 may be provided so as to illuminate a fundus Ef of the subject's eye by illumination light via the mirror portion 22b of the hole mirror and the objective lens 25. The illumination light may be either one of visible light and infrared light. The illumination optical system 10 may include a visible light illumination optical system that illuminates the fundus Ef by the visible light, and an infrared light illumination optical system that illuminates the fundus Ef by the infrared light. The illumination optical system 10 includes a photography light source 14 and an observation light source 11, and may be provided so as to illuminate the fundus Ef by either one of the photography light source 14 and the observation light source 11. For example, a flashlamp or an LED which emits the visible light may be used as the photography light source 14, and a halogen lamp or an infrared LED which emits the infrared light may be used as the observation light source 11.

The photography optical system 30 may be provided so as to photograph a front image of the fundus Ef illuminated by the illumination light of the illumination optical system 10 via the opening 22a of the hole mirror 22. The photography optical system 30 may include a visible light photography optical system that photographs a front image of the fundus of the subject's eye illuminated by the visible light, and an infrared light photography optical system that photographs a front image of the fundus of the subject's eye illuminated by the infrared light. The photography optical system 30 may include a two-dimensional imaging element (an imaging element for photography) 35 that is disposed conjugately with the fundus and receives reflected light from the fundus. The photography optical system 30 may include a focusing lens 32 and the two-dimensional imaging element 35. The focusing lens 32 moves in an optical axis direction so as to adjust focus on the subject's eye. The photography optical system 30 may include a two-dimensional imaging element (an imaging element for observation) 38 that is disposed conjugately with the fundus and receives reflected light from the fundus. The imaging element for photography and the imaging element for observation may be formed of the same imaging element.

The photography optical system 30 may include a first imaging element (for example, the two-dimensional imaging element 35) that photographs a still image of the fundus, and a second imaging element (for example, the two-dimensional imaging element 38) for observing the fundus in a moving picture mode. Here, an imaging element different from the first imaging element may be used in the second imaging element.

The coherence optical system (the OCT optical system) 200 may be provided so as to obtain a tomographic image of the fundus of the subject's eye via the objective lens 25 using optical coherence tomography.

More specifically, the coherence optical system 200 mainly includes a light source 102; a detector 120; and a scanning unit 108. The detector 120 detects a state of coherence between measurement light which illuminates a subject's eye E, and reference light. The measurement light is emitted from the light source 102, and is guided to the fundus Ef via a measurement optical path. The reference light is emitted from the light source 102, and is guided to the detector 120 via a reference optical path.

The scanning unit 108 is disposed on the measurement optical path, and scans the measurement light on the subject's eye E. The scanning unit 108 may repeatedly scan the measurement light on the subject's eye E.

The device 1 can obtain a tomographic image of the subject's eye E based on a detection signal from the detector 120 at each scanning position of the scanning unit 108.
<Anterior Chamber Observation Optical System>

The device 1 may be provided with an anterior chamber observation optical system 60 for observing a front image of an anterior chamber. The anterior chamber observation optical system 60 may be provided so as to observe an anterior chamber observation image of the subject's eye illuminated by an anterior chamber illumination light source 58 via the objective lens 25. For example, the anterior chamber observation optical system 60 may include a relay lens 64 that concentrates reflected light from the anterior chamber, and a two-dimensional imaging element 65 that is disposed conjugately with the anterior chamber and collects reflected light from the anterior chamber. For example, an infrared light source may be used as the anterior chamber illumination light source 58.
<Combination of Anterior Chamber Observation Optical System and OCT Optical System for Fundus Camera Optical System Using Wavelength Separation Member (Wavelength Selective Splitter)>

A first wavelength separation member (for example, a dichroic mirror 24) is provided so that a first optical axis L1 commonly shared by the illumination optical system 10 and the photography optical system 30 can be set coaxial with a second optical axis L2 commonly shared by the coherence optical system 200 and the anterior chamber observation optical system 60. The first wavelength separation member is disposed between the objective lens 25 and the hole mirror 22.

A second wavelength separation member (for example, a dichroic mirror 61) is provided so that the second optical axis L2 can be formed by setting an optical axis L3 of the OCT optical system to be coaxial with an optical axis L4 of the anterior chamber observation optical system 60.

The above-mentioned wavelength separation member may be a flat plate-like dichroic mirror, or a dichroic prism.

For example, in this configuration, when a front image of the fundus (for example, a color fundus image) is captured, and when a tomographic image of the fundus is captured, it is possible to perform alignment using a front image of the anterior chamber. Accordingly, a compound device of the fundus camera and the OCT can smoothly perform alignment with respect to the subject's eye.

In another aspect, in the compound device of the fundus camera and the OCT, the anterior chamber observation optical system is provided without deteriorating the respective functions of the fundus camera and the OCT. Accordingly, it is possible to properly photograph an image with each of the fundus camera and the OCT, and it is possible to smoothly perform the alignment with respect to the subject's eye.

In addition, it is easy to notice an axis deviation associated with the dichroic mirror 24. For example, in a case where position alignment with respect to the eye is completed using the photography optical system 30 (for example, a working dot W may be used), and when an alignment index on the anterior chamber observation image deviates from a reference position, it is recognized that there is also an axis deviation present in the coherence optical system 200. Accordingly, it is possible to smoothly perform maintenance.

Hereinafter, a first example of the wavelength-selective characteristics of the wavelength separation member will be described. For example, the light source (the measurement light source) 102 of the coherence optical system 200 may be a light source that emits light having a center wavelength $\lambda$ (for example, $\lambda=840$ nm, $\lambda=870$ nm, or $\lambda=880$ nm) between 800 nm and 900 nm. For example, the light source used may have a wavelength bandwidth of ±30 nm to ±60 nm around the center wavelength. Alternatively, a wide bandwidth light source may be used. In the following example, a light source having an emitted wavelength $\lambda$ of 840 nm to 920 nm is used as the light source 102.

For example, the anterior chamber illumination light source 58 may be a light source that emits light having a center wavelength $\lambda$ between 900 nm and 1000 nm (more preferably, between 940 nm and 1000 nm). In this case, the center wavelength of the anterior chamber illumination light source 58 may be set to have a wavelength bandwidth longer than the emitted wavelength of the light source 102.

Illumination light sources of the illumination optical system 10 may be the observation light source 11 that emits light having a center wavelength $\lambda$ between 750 nm and 800 nm (more preferably, between 770 nm and 790 nm), and the photography light source 14 that emits light having a visible bandwidth $\lambda$ less than 750 nm. The center wavelength of the observation light source 11 may be set to have a wavelength bandwidth shorter than the emitted wavelength of the light source 102. In the following example, a light source having an emitted wavelength $\lambda$ of 750 nm to 800 nm is used as the light source 11. The photography light source 14 may be a light source that emits light containing a wavelength $\lambda$ in a range of 400 nm to 700 nm (in the following example, in a range of 400 nm to 750 nm). The wavelength bandwidth of light emitted from each of the light sources may be limited by a cut filter configured to cut off a predetermined wavelength.

For example, the first wavelength separation member (for example, the dichroic mirror 24) has a cut-on wavelength $\lambda$ set between 760 nm and 840 nm, and has wavelength-selective characteristics by which at least fundus observation light from the observation light source 11 is allowed to transmit therethrough, and measurement light from the light source 102 of the coherence optical system 200 and light from the anterior chamber illumination light source 58 is reflected. In this case, the first wavelength separation member may also be configured to allow a majority of the fundus observation light from the observation light source 11 to transmit therethrough, and to reflect a majority of the measurement light from the light source 102 and a majority of the light from the anterior chamber illumination light source 58. The term "a majority of light" implies the entirety of light of 90% or greater.

For example, the second wavelength separation member (for example, the dichroic mirror 61) has a cut-on wavelength (or a cut-off wavelength) $\lambda$ set between 900 nm and 1000 nm (preferably, between 930 nm and 970 nm), and has wavelength-selective characteristics by which the measurement light from the light source 102 of the coherence optical system 200 is separated from the anterior chamber observation light from the anterior chamber illumination light source 58. The second wavelength separation member may allow the measurement light to transmit therethrough, and reflect the anterior chamber observation light, or the second wavelength separation member may reflect the measurement light, and allow the anterior chamber observation light to transmit therethrough. In this case, the second wavelength separation member may also be configured such that a majority of the measurement light from the light source 102 of the coherence optical system 200 is separated from a majority of the anterior chamber observation light from the anterior chamber illumination light source 58.

In this configuration, also, when the light source (the measurement light source) 102 of the coherence optical system 200 has a wavelength bandwidth $\lambda$ of 750 nm to 900 nm (more preferably, a wavelength bandwidth $\lambda$ of 800 nm to 900 nm), it is possible to well observe the anterior chamber in addition to the photography and the observation of the fundus.

The first wavelength separation member may have wavelength characteristics by which fundus photography light from the photography light source 14 is allowed to transmit therethrough. Instead, the first wavelength separation member may deviate from an optical path of the photography optical system 30 when an image of the fundus is photographed using the photography light source 14.

In the optical system, an index light source (an alignment light source) 55 may be provided while being disposed conjugately with (for example, at the position of the opening 22a of the hole mirror 22) the anterior chamber. The index light source 55 may be disposed in an optical system in a device housing. An alignment index from the index light source 55 is reflected by the anterior chamber of the subject's eye, and then is received by the two-dimensional imaging element (the imaging element for observation) 35 (imaging sensor). The alignment index (that is, the working dot W) received by the two-dimensional imaging element 35 is observed by an inspector, and is used for the fine adjustment of alignment with respect to the subject's eye.

For example, the index light source 55 may be a light source that emits light having a center wavelength longer than that of light from the observation light source 11, and shorter than that of light from the light source 102 of the coherence optical system 200. More preferably, the index light source 55 is a light source that emits light having a center wavelength λ between 780 nm and 815 nm.

The first wavelength separation member may have wavelength characteristics by which light from the index light source 55 is allowed to transmit therethrough. More preferably, the first wavelength separation member has a cut-on wavelength λ set between 780 nm and 815 nm.

In addition to the optical systems, a focus index projection optical system (hereinafter, a projection optical system) 40 may be provided, which projects a focus index (for example, a split index) on the fundus. The focus index is used so as to manually or automatically adjust focus on the subject's eye. For example, the projection optical system 40 uses a light source that emits light having a center wavelength similar to that of light from the observation light source 11 (for example, the center wavelength λ is set between 765 nm and 785 nm). The first wavelength separation member may have wavelength characteristics by which focus index light is allowed to transmit therethrough.

In addition to the optical systems, an alignment index projection optical system (hereinafter, a projection optical system) 50 may be provided. The projection optical system 50 projects an alignment index to the anterior chamber of the subject's eye from an outer side of the objective lens 25. An image of the alignment index is captured by the anterior chamber observation optical system 60, and is used for the automatic alignment or the manual alignment using the anterior chamber image. For example, the projection optical system 50 uses a light source that emits light having a center wavelength similar to that of light from the anterior chamber illumination light source 75 (for example, the center wavelength λ is set between 900 nm and 1000 nm). The first wavelength separation member may have wavelength characteristics by which the alignment index is allowed to transmit therethrough.

At least any one of the index light source 55, the projection optical system 40, and the projection optical system 50 may be disposed in the optical system of the device. The entirety of the index light source 55, the projection optical system 40, and the projection optical system 50 may be disposed in the optical system of the device.

Hereinafter, a second example of the wavelength-selective characteristics of the wavelength separation member will be described. For example, the light source (the measurement light source) 102 of the coherence optical system 200 may be a light source that emits light having a center wavelength λ between 1000 nm and 1350 nm (more preferably, between 1050 nm and 1300 nm). The light source 102 is a wavelength sweep light source, and an SS-OCT optical system may be used as the coherence optical system 200. For example, the light source used may have a wavelength bandwidth of ±30 nm to ±60 nm around the center wavelength. Alternatively, a wide bandwidth light source may be used.

For example, the anterior chamber illumination light source 58 may be a light source that emits light having a center wavelength λ between 900 nm and 1000 nm (more preferably, between 940 nm and 1000 nm). In this case, the center wavelength of the anterior chamber illumination light source 58 may be set to have a wavelength bandwidth shorter than the emitted wavelength of the light source 102.

The illumination light sources may be the observation light source 11 that emits light having a center wavelength λ between 750 nm and 900 nm (more preferably, between 800 nm and 900 nm), and the photography light source 14 that emits light having a visible bandwidth λ less than 750 nm. More specifically, the photography light source 14 may be a light source that emits light containing a visible wavelength λ in a range of 400 nm to 700 nm (in the following example, in a range of 400 nm to 750 nm). The wavelength bandwidth of light emitted from each of the light sources may be limited by a cut filter configured to cut off a predetermined wavelength.

For example, the (first) dichroic mirror 24 has a cut-on wavelength λ set between 760 nm and 900 nm, and has wavelength-selective characteristics by which at least fundus observation light from the observation light source 11 is allowed to transmit therethrough, and measurement light from the light source 102 of the coherence optical system 100 and light from the anterior chamber illumination light source 58 are reflected.

For example, the (second) dichroic mirror 61 has a cut-on wavelength (or a cut-off wavelength) λ set between 950 nm and 1050 nm, and has wavelength-selective characteristics by which the measurement light from the light source 102 of the coherence the optical system 200 is separated from the anterior chamber observation light from the anterior chamber illumination light source 58. The dichroic mirror 61 may allow the measurement light to transmit therethrough, and reflect the anterior chamber observation light, or the dichroic mirror 61 may reflect the measurement light, and allow the anterior chamber observation light to transmit therethrough.

In this configuration, since it is possible to use anterior chamber observation light having a wavelength bandwidth λ of 800 nm to 900 nm, it is possible to reduce a burden on the subject's eye.

<Cut Filter>

The anterior chamber observation optical system 60 may have a cut filter 67 provided on an optical path on a downstream side of the dichroic mirror 61, and the cut filter 67 cuts off light having a wavelength bandwidth corresponding to the measurement light of the coherence optical system 200. Since the cut filter can cut off the measurement light of the coherence optical system 200, it is possible to well observe the anterior chamber.

For example, the cut filter is disposed between the dichroic mirror 61 and the two-dimensional imaging element 65. In addition, the relay lens 64 disposed between the second dichroic mirror and the two-dimensional imaging element may be coated with the cut filter. The cut filter may be disposed separately from the relay lens 64.

The photography optical system 30 may also be provided with a cut filter that cuts off light having a wavelength bandwidth corresponding to the measurement light of the coherence optical system 200.

<Fluorescence Photography Function>

The device may be configured to acquire a fluorescent fundus image produced by fluorescence from the fundus of the subject's eye. An exciter filter EX is insertably and removably disposed on an optical path of the illumination optical system 10, and has wavelength-selective characteristics by which fluorescence excitation light of the light from the photography light source 14 is allowed to transmit therethrough, and light having wavelengths other than that of the fluorescence excitation light is cut off. For example, the exciter filter EX is provided between the photography light source 14 and the hole mirror 22, and is inserted and retracted by the driving of an insertion and removal mechanism A.

A barrier filter BA is insertably and removably disposed on the optical path of the photography optical system 30, and has wavelength-selective characteristics by which fluorescence from the fundus excited by the fluorescence excitation light is allowed to transmit therethrough, and light having wavelengths other than that of the fluorescence is cut off. For example, the barrier filter BA is provided between the hole mirror 22 and the imaging element 35, and is inserted and retracted by the driving of an insertion and removal mechanism B. More preferably, the barrier filter BA may be provided between a dichroic filter 37 and the two-dimensional imaging element 35 so as to prevent the barrier filter BA from adversely affecting the observation of the fundus.

The wavelength-selective characteristics of each of the exciter filter EX and the barrier filter BA may be set so as to photograph a fluorescent fundus image using autofluorescence from the subject's eye. That is, the exciter filter EX and the barrier filter BA may be used in conditions in which a fluorescent agent is not intravenously injected into the subject, or may be filters that optically extract self-emitting fluorescent components by exciting the fundus with light having a specific wavelength.

For example, a filter configured to obtain red color fluorescence from the fundus by using green color light as excitation light is used as a filter for autofluorescence photography. The exciter filter EX may have wavelength-selective characteristics by which green color light (for example, light having a bandwidth $\lambda$ of 500 nm to 600 nm) is allowed to transmit therethrough, and other light is shut off. The barrier filter BA may have wavelength-selective characteristics by which red color light (for example, light having a bandwidth $\lambda$ of 625 nm to 760 nm) is allowed to transmit therethrough, and other light is shut off. The exciter filter EX may have wavelength-selective characteristics by which the exciter filter EX allows the green color light (for example, light having a bandwidth $\lambda$ of 500 nm to 600 nm) and light having a bandwidth $\lambda$ of 800 nm or greater to transmit therethrough, and shuts off other light. The reason for this is that as a result, emitted light from the photography light source 14 does not contain light having a bandwidth $\lambda$ of 800 nm or greater, and the subject's eye is not illuminated with light other than the excitation light.

The exciter filter EX is not limited to a filter through which green color light is allowed to transmit. For example, the exciter filter EX may have wavelength-selective characteristics by which blue color light is allowed to transmit therethrough, and other light is shut off. A photography light source that emits excitation light may be provided instead of the exciter filter.

The barrier filter BA may have wavelength-selective characteristics by which red color light (for example, light having a bandwidth $\lambda$ of 625 nm to 760 nm) is allowed to transmit therethrough, and other light is shut off. A filter for autofluorescence photography is not limited to the above-mentioned filter. For example, the barrier filter BA may be configured such that light (for example, yellow color light) having a wavelength shorter than that of a red color component is also allowed to transmit therethrough, and other light is shut off. The barrier filter BA may be configured such that light (for example, near-infrared light) having a wavelength longer than that of a red color component is also allowed to transmit therethrough, and other light is shut off.

The barrier filter BA may have wavelength-selective characteristics by which fluorescence from the fundus Ef is allowed to transmit therethrough, the fluorescence containing first light (first fluorescence) having a wavelength bandwidth $\lambda$ (for example, a wavelength bandwidth $\lambda$ of 625 nm to 700 nm) less than 700 nm and second light (second fluorescence) having a wavelength bandwidth $\lambda$ (for example, a wavelength bandwidth $\lambda$ of 700 nm to 750 nm) greater than 700 nm and longer than that of the fundus observation light from the observation light source 11.

<Barrier Filter for Color Photography>

A second barrier filter BA may be provided separately from the barrier filter (a first barrier filter) BA for fluorescence photography, and is inserted on the optical path when an image of the fundus of the subject's eye is photographed in color. The second barrier filter BA is insertably and removably disposed on the optical path of the photography optical system 30, and has wavelength-selective characteristics by which light from the photography light source 14 is reflected by the fundus, light (for example, light having a visible bandwidth containing red color light, blue color light, and green color light) having a visible bandwidth necessary for color photography is allowed to transmit therethrough, and light (for example, light having an infrared bandwidth) unnecessary for color photography is cut off. An upper limit of a transmitted wavelength bandwidth of the second barrier filter BA is set to be less than that of the barrier filter BA for fluorescence photography. For example, the upper limit $\lambda$ of the transmitted wavelength of the first barrier filter is set to 750 nm, and the upper limit $\lambda$ of the transmitted wavelength of the second barrier filter is set to 700 nm.

In this configuration, when fluorescence photography is performed, the first barrier filter is selectively inserted on the optical path, and when color photography is performed, the second barrier filter is selectively inserted on the optical path. As a result, a fluorescent fundus image and a color fundus image are well photographed.

<Wavelength Separation Member Taken into Consideration for Fluorescence Photography>

The photography optical system 30 may have a wavelength separation member (for example, the dichroic mirror 37) that is disposed on the optical path of the photography optical system 30 and divides the optical path of the photography optical system 30 into a first photographic optical path and a second photographic optical path.

The first photographic optical path may be an optical path through which fundus-reflected light produced by the photography light source 14 and fluorescence are guided to the first imaging element (for example, the two-dimensional imaging element 35), and the second photographic optical path may be an optical path through which fundus-reflected light produced by the observation light source 11 is guided to the second imaging element (for example, the two-dimensional imaging element 38).

The wavelength-selective characteristics of the wavelength separation member (for example, the dichroic mirror 37) for dividing the optical path into the first photographic optical path and the second photographic optical path may be set in such a manner that the fundus-reflected light produced by the photography light source 14 and the fluorescence containing the first light and the second light are guided to the first imaging element (for example, the two-dimensional imaging element 35), and the fundus observation light from the observation light source 11 is guided to the second imaging element (for example, the two-dimensional imaging element 38).

More specifically, the wavelength separation member (for example, the dichroic mirror 37) for dividing the optical path into the first photographic optical path and the second photographic optical path may have wavelength-selective characteristics by which the fundus-reflected light produced by the photography light source 14 and the fluorescence containing the first light and the second light are allowed to transmit therethrough, and the fundus observation light from the observation light source 11 is reflected. In this case, the wavelength-selective characteristics of the wavelength separation member (for example, the dichroic mirror 37) for dividing the optical path into the first photographic optical path and the second photographic optical path may also be configured to allow a majority of the fundus-reflected light produced by the photography light source 14 and a majority of the fluorescence containing the first light and the second light to transmit therethrough, and to reflect a majority of the fundus observation light from the observation light source 11. The term "a majority of light" implies the entirety of light of 90% or greater.

The wavelength separation member (for example, the dichroic mirror 37) for dividing the optical path into the first photographic optical path and the second photographic optical path may have wavelength-selective characteristics by which the fundus-reflected light produced by the photography light source 14 and the fluorescence containing the first light and the second light are reflected, and the fundus observation light from the observation light source 11 is allowed to transmit therethrough.

The wavelength-selective characteristics of the wavelength separation member (for example, the dichroic mirror 37) for dividing the optical path into the first photographic optical path and the second photographic optical path may also be configured to reflect a majority of the fundus-reflected light produced by the photography light source 14 and a majority of the fluorescence containing the first light and the second light, and to allow a majority of the fundus observation light from the observation light source 11 to transmit therethrough. The term "a majority of light" implies the entirety of light of 90% or greater.

At this time, a light source configured to emit light having a center wavelength λ between 800 nm to 900 nm is used as the light source 102 of the coherence optical system 200, a light source configured to emit light having a visible bandwidth containing the first light and the second light is used as the photography light source 14, and an observation light source configured to emit light a center wavelength λ between 750 nm to 800 nm is used as the observation light source 11.

The wavelength separation member (for example, the dichroic mirror 37) for dividing the optical path into the first photographic optical path and the second photographic optical path may have a cut-on wavelength (or a cut-off wavelength) λ set between 725 nm and 775 nm, and have wavelength-selective characteristics by which the fundus-reflected light produced by the photography light source 14 and the fluorescence containing the first light and the second light are guided to the first imaging element, and the fundus observation light from the observation light source 11 is guided to the second imaging element.

With these wavelength-selective characteristics, it is possible to photograph a fluorescent image produced by fundus fluorescence that contains the first light (so-called visible light) having a wavelength λ less than 700 nm and the second light (so-called infrared light) having a wavelength greater than 700 nm and shorter than that of the fundus observation light from the observation light source. As a result, with the compound device of the OCT and the fundus camera, it is possible to acquire a good fluorescent image. For example, since a lipofuscin reaction also occurs in wavelength components λ greater than 700 nm when autofluorescence photography is performed, it is possible to acquire a clinically useful autofluorescence image by introducing the wavelength components. The amount of autofluorescence from the fundus is very small, and it is possible to compensate for a deficient amount of light in the fluorescence image by introducing the second light having a wavelength λ greater than 700 nm in addition the first light having a wavelength λ less than 700 nm.

More preferably, the wavelength-selective characteristics of the wavelength separation member (for example, the dichroic mirror 37) for dividing the optical path into the first photographic optical path and the second photographic optical path are set in such a manner that at least 90% or greater light having a wavelength λ of 700 nm is guided to the first imaging element (for example, the two-dimensional imaging element 35), and at least 70% or greater light having a wavelength λ of 750 nm is shut off. Accordingly, it is possible to sufficiently extract light having a wavelength λ greater than 700 nm, and to shut off the fundus observation light from the observation light source well (refer to FIG. 8).

More preferably, the wavelength-selective characteristics of the wavelength separation member (for example, the dichroic mirror 37) for dividing the optical path into the first photographic optical path and the second photographic optical path are set in such a manner that at least 90% or greater light having a wavelength λ of 720 nm is guided to the first imaging element (for example, the two-dimensional imaging element 35), and at least 70% or greater light having a wavelength λ of 750 nm is shut off. Accordingly, it is possible to sufficiently extract light having a wavelength λ greater than 700 nm, and to shut off the fundus observation light from the observation light source well (refer to FIG. 8).

<Fluorescence Photography Mode>

For example, the device may be provided with a mode setting switch for setting either one of a color photography mode and a fluorescence photography mode, and a color front image of the fundus of the subject's eye is obtained in the color photography mode, and a fluorescent front image of the fundus of the subject's eye is obtained in the fluorescence photography mode. In a case where the fluorescence photography mode is set, and when an image of the fundus is photographed, a control unit 70 inserts the exciter filter EX and the barrier filter BA on the respective optical paths, and controls the photography light source 14 to emit light.

Visible light from the photography light source 14 is limited to fluorescence excitation light by the exciter filter EX, and the subject's eye is illuminated by the fluorescence excitation light. The fundus-reflected light produced by the excitation light is shut off by the barrier filter BA. Here, fluorescence produced by a radiocontrast agent or autofluorescence is emitted from the fundus. The fluorescence from the fundus passes through the barrier filter BA via the objective lens 25 to the dichroic mirror 37. Accordingly, a fluorescent fundus image of fluorescence flux is captured. The captured fluorescent image is stored in a memory 72, and is displayed on a display unit 75.

For example, when the autofluorescence photography is performed, fluorescence from lipofuscin contained in the fundus tissue is emitted from the fundus due to the fluorescence excitation light having a green color light as a main component. Accordingly, an autofluorescent fundus image of fluorescence flux is captured.

<Example>

As illustrated in FIG. 1(*a*), a device main body 1 in this example mainly includes a base 4; a photography unit 3; a face support unit 5; and an operation unit 74. The photography unit 3 may accommodate an optical system (to be described later). The photography unit 3 may be provided so as to able to move with respect to the subject's eye E in three-dimensional directions (X, Y, and Z directions). The face support unit 5 may be fixed to the base 4 so as to support a subject's face.

An XYZ drive unit 6 may move the photography unit 3 relative to the eye E in a lateral direction, a vertical direction (the Y direction), and a forward and backward direction. The photography unit 3 may move with respect to the right and left eyes in the lateral direction (the X direction) and the forward and backward (operation distance) direction (the Z direction) due to the movement of a moving base 2 with respect to the base 4.

A joystick 74a is an operation member operated by an inspector so as to move the photography unit 3 with respect to the eye E. Naturally, the operation member is not limited to the joystick 74a, and another operation member (for example, a touch panel or a trackball) may be adopted.

For example, the operation unit transmits an operation signal from the inspector to the control unit 70. At this time, the control unit 70 may send the operation signal to a personal computer 90 (to be described later). For example, the personal computer 90 sends a control signal to the control unit 70 in response to the operation signal. When the control unit receives the control signal, the control unit performs various control operations.

The moving base 2 moves with respect to the subject's eye by the operation of the joystick 74a. When a rotating knob 74b is rotated, the XYZ drive unit 6 is Y driven, and the photography unit 3 moves in the Y direction. In a case where the moving base 2 is not provided, the XYZ drive unit 6 may be configured to move the photography unit 3 with respect to the subject's eye when the joystick 74a is operated.

The photography unit 3 may be provided with the display unit 75 (for example, the display unit 75 is disposed so as to face the inspector). The display unit 75 may display a fundus observation image, a fundus photographic image, an anterior chamber observation image, or the like.

The device main body 1 in this example is connected to the personal computer (hereinafter, a PC) 90. For example, the display unit 95 and operation members (for example, a keyboard 96 and a mouse 97) may be connected to the PC 90.

Figure 2:
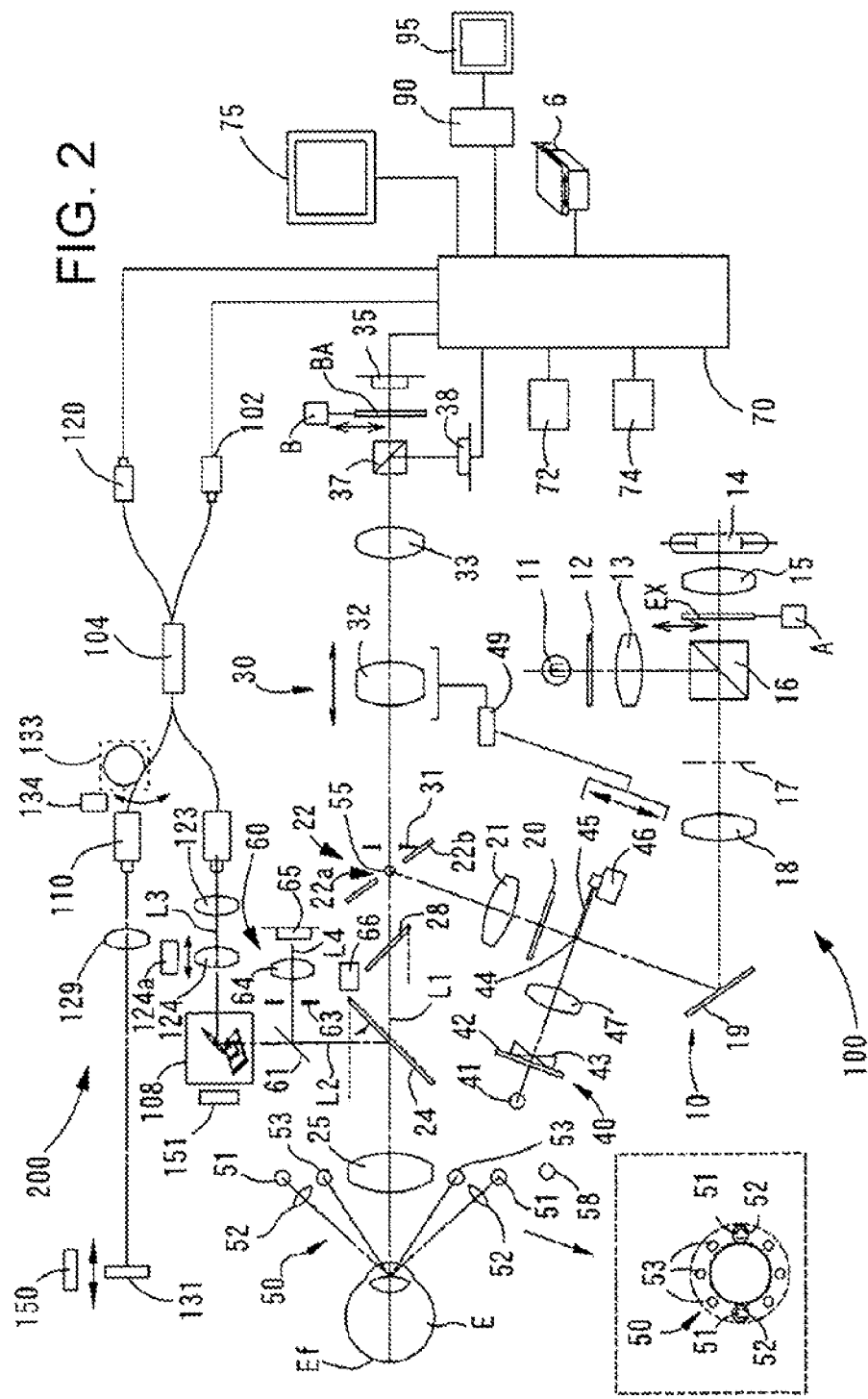
FIG. 2 is a view illustrating an optical system and a control system of the fundus photography device according to the embodiment.

As illustrated in FIG. 2, the optical system in this example mainly includes the illumination optical system 10; the photography optical system 30; and the coherence optical system (hereinafter, also referred to as an OCT optical system) 200. The optical system may further include the focus index projection optical system 40; the alignment index projection optical system 50; and the anterior chamber observation optical system 60. The illumination optical system 10 and the photography optical system 30 are used as a fundus camera optical system 100 that obtains a color fundus image by photographing the fundus using visible light (for example, a non-mydriatic state). The photography optical system 30 captures an image of the fundus of the subject's eye. The OCT optical system 200 obtains non-invasively a tomographic image of the fundus of the subject's eye by using optical coherence tomography.

<Fundus Camera Optical System>

Hereinafter, an example of an optical disposition of the fundus camera optical system 100 will be described.

<Illumination Optical System>

For example, the illumination optical system 10 has an observation illumination optical system and a photography illumination optical system. The photography illumination optical system mainly includes the photography light source 14; a condensing lens 15; a ring slit 17; a relay lens 18; a mirror 19; a black point plate 20; a relay lens 21; the hole mirror 22, and the objective lens 25. A flashlamp, an LED, or the like may be used as the photography light source 14. The black point plate 20 has a black point in a center portion thereof. The photography light source 14 is used so as to photograph the fundus of the subject's eye using light in a visible bandwidth.

The observation illumination optical system mainly includes the observation light source 11, an infrared filter 12, a condensing lens 13, a dichroic mirror 16, and the optical system from the ring slit 17 to the objective lens 25. A halogen lamp, an LED, or the like may be used as the observation light source 11. For example, the observation light source 11 is used so as to observe the fundus of the subject's eye using light in a near-infrared bandwidth. The infrared filter 12 is provided so as to allow near-infrared light having a wavelength of 750 nm or greater to transmit therethrough, and to cut off light having a wavelength less than 750 nm. The dichroic mirror 16 is disposed between the condensing lens 13 and the ring slit 17. The dichroic mirror 16 has characteristics of reflecting light from the observation light source 11, and allowing light from the photography light source 14 to transmit therethrough. The observation light source 11 and the photography light source 14 may be disposed in series on the same optical axis.

<Photography Optical System>

For example, the objective lens 25, a photographic diaphragm 31, the focusing lens 32, an imaging lens 33, and the imaging element 35 are mainly disposed in the photography optical system 30. The photographic diaphragm 31 is positioned in the vicinity of an opening of the hole mirror 22. The focusing lens 32 can move in the optical axis direction. The imaging element 35 can be used for sensitive photography in a visible bandwidth. The photographic diaphragm 31 is disposed substantially conjugately with the pupil of the subject's eye E with respect to the objective lens 25. The focusing lens 32 is moved in the optical axis direction by the driving of a moving mechanism 49 equipped with a motor.

The dichroic mirror 37 is disposed between the imaging lens 33 and the imaging element 35, and has characteristics of reflecting infrared light and a part of visible light and allowing a majority of visible light to transmit therethrough. The observation imaging element 38 having sensitivity in an infrared bandwidth is disposed in a reflection direction of the dichroic mirror 37. A flip-up mirror may be used in place of the dichroic mirror 34. For example, the flip-up mirror is inserted on the optical path when the fundus is observed, and is retracted when an image of the fundus is photographed.

The insertable and removable dichroic mirror (a wavelength selective mirror) 24 as an optical path division member is diagonally provided between the objective lens 25 and the hole mirror 22. The dichroic mirror 24 reflects the wavelength light of OCT measurement light and the wavelength light (for example, light having a center wavelength λ of 940 nm) from the alignment index projection optical system 50 and the anterior chamber illumination light source 58. The dichroic mirror 24 has characteristics of allowing light having a wavelength of 800 nm or less to transmit therethrough, the light containing the wavelength (for example, the center wavelength of 780 nm) of the fundus observation illumination light source. The dichroic mirror 24 is flipped up during the photography in conjunction with the driving of an insertion and removal mechanism 66, and is retracted out of the optical path. The insertion and removal mechanism 66 can be configured to include a solenoid, a cam, and the like.

Optical path corrective glass 28 is disposed closer to the imaging element 35 than the dichroic mirror 24, and can be flipped up by the driving of the insertion and removal mechanism 66. The optical path corrective glass 28 serves to correct the position of the optical axis L1 shifted by the dichroic mirror 24, when being inserted on the optical path.

Luminous flux emitted from the observation light source 11 is transformed into infrared luminous flux by the infrared filter 12, and the infrared luminous flux is reflected by the condensing lens 13 and the dichroic mirror 16, and illuminates the ring slit 17. The light that transmits through the ring slit 17 reaches the hole mirror 22 via the relay lens 18, the mirror 19, the black point plate 20, and the relay lens 21. The light reflected by the hole mirror 22 transmits through the corrective glass 28 and the dichroic mirror 24, and after the light is converged in the vicinity of the pupil of the subject's eye E by the objective lens 25, the light disperses and illuminates the anterior chamber of the subject's eye.

The reflected light from the fundus is imaged on the imaging element 38 via the objective lens 25, the dichroic mirror 24, the corrective glass 28, the opening of the hole mirror 22, the photographic diaphragm 31, the focusing lens 32, the imaging lens 33, and the dichroic mirror 37. The imaging element 38 is disposed conjugately with the fundus. An output from the imaging element 38 is input to the control unit 70, and the control unit 70 displays a fundus observation image (a fundus front observation image) 82 of the subject's eye photographed by the imaging element 38 on the display unit 75 (refer to FIG. 3).

Luminous flux emitted from the photography light source 14 transmits through the dichroic mirror 16 via the condensing lens 15. Thereafter, the fundus is illuminated by visible light via the same optical path as that of the illumination light for the observation of the fundus. The reflected light from the fundus is imaged on the imaging element 35 via the objective lens 25, the opening of the hole mirror 22, the photographic diaphragm 31, the focusing lens 32, and the imaging lens 33.

<Focus Index Projection Optical System>

The focus index projection optical system 40 mainly includes an infrared light source 41; a slit index plate 42; two declination prisms 43; a projection lens 47; and a spot mirror 44 diagonally provided on the optical path of the illumination optical system 10. The two declination prisms 43 are attached to the slit index plate 42. The spot mirror 44 is diagonally provided on the optical path of the illumination optical system 10. The spot mirror 44 is fixedly attached to the tip of a lever 45. Typically, the spot mirror 44 is provided diagonally with respect to the optical axis, and is retracted out of the optical path at a predetermined time before the photography by the rotation of the shaft of a rotary solenoid 46.

The spot mirror 44 is disposed conjugately with the fundus of the subject's eye E. The light source 41, the slit index plate 42, the declination prisms 43, the projection lens 47, the spot mirror 44, and the lever 45 are moved in the optical axis direction in conjunction with the focusing lens 32 by the driving of the moving mechanism 49. After luminous flux from the slit index plate 42 of the focus index projection optical system 40 is reflected by the spot mirror 44 via the declination prisms 43 and the projection lens 47, the luminous flux is projected on the fundus of the subject's eye E via the relay lens 21, the hole mirror 22, the dichroic mirror 24, and the objective lens 25. When the fundus is not in focus, index images S1 and S2 are projected on the fundus while being separated from each other in response to a deviation direction and the amount of deviation. In contrast, when the fundus is in focus, the index images S1 and S2 are projected on the fundus while matching each other (refer to FIG. 5). The index images S1 and S2 are captured along with a fundus image by the imaging element 38.

<Alignment Index Projection Optical System>

As illustrated in a dotted line box on the left in FIG. 2, the alignment index projection optical system 50 configured to project alignment index luminous flux has a plurality of infrared light sources disposed at 45 degree intervals concentrically about the photography optical axis L1. An ophthalmic photography device in this example mainly includes a first index projection optical system (at 0 degrees and 180 degrees) and a second index projection optical system. The first index projection optical system has an infrared light source 51 and a collimating lens 52. The second index projection optical system is disposed at a position different from that of the first index projection optical system, and has six infrared light sources 53. The infrared light sources 51 are disposed to be bilaterally symmetrical while a perpendicular plane passing through the photography optical axis L1 is interposed between the infrared light sources 51. In this case, the first index projection optical system laterally projects infinite indexes on a cornea of the subject's eye E. The second index projection optical system is configured to vertically or diagonally project finite indexes on the cornea of the subject's eye E. FIG. 2 illustrates the first index projection optical system (at 0 degrees and 180 degrees) and only a part of the second index projection optical system (at 45 degrees and 135 degrees) for illustrative purposes.

<Anterior Chamber Observation Optical System>

The anterior chamber observation (photography) optical system 60 configured to photograph the anterior chamber of the subject's eye mainly includes the dichroic mirror 61, a diaphragm 63, the relay lens 64, and the two-dimensional imaging element 65 (a photodetector: hereinafter, may be briefly referred to as the imaging element 65) on a reflection side of the dichroic mirror 24. The imaging element 65 has sensitivity in an infrared bandwidth. The imaging element 65 also acts as imaging means for the detection of an alignment index, and captures an image of the anterior chamber illuminated by infrared light emitted from the anterior chamber illumination light source 58 and an image of the alignment index. The anterior chamber illuminated by the anterior chamber illumination light source 58 is received by the imaging element 65 via the objective lens 25, the dichroic mirror 24, and the optical system from the dichroic mirror 61 to the relay lens 64. Alignment luminous flux emitted from the light source of the alignment index projection optical system 50 is projected on the cornea of the subject's eye. The cornea-reflected image is received (projected on) by the imaging element 65 via the objective lens 25 to the relay lens 64.

Figure 4A:
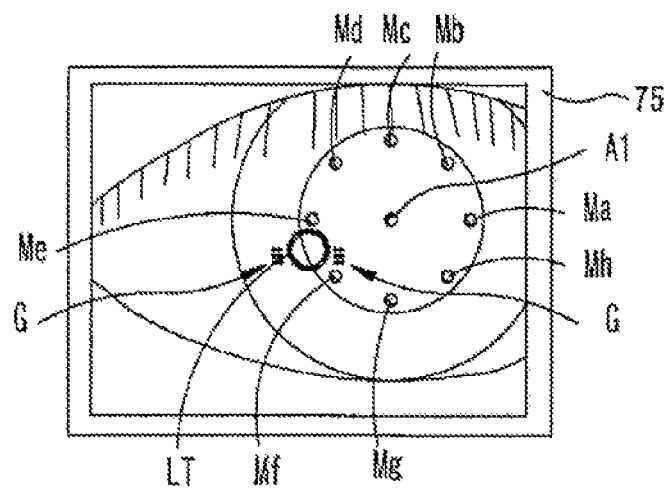
FIGS. 4A and 4B illustrate examples in which an anterior chamber image captured by an imaging element is displayed on the display unit.
Figure 4B:
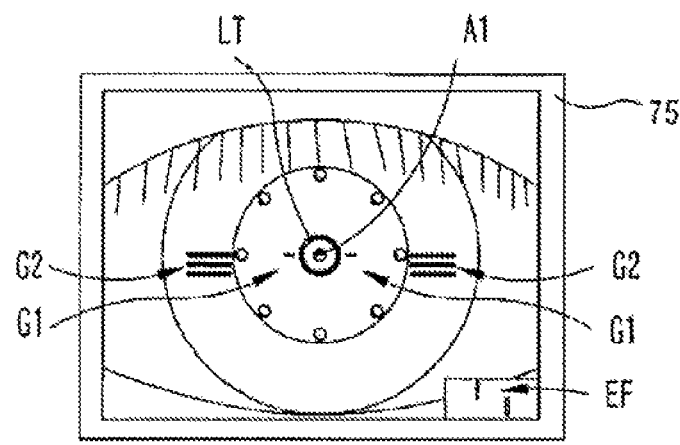

An output from the two-dimensional imaging element 65 is input to the control unit 70, and as illustrated in FIG. 4, the display unit 75 displays an anterior chamber image captured by the two-dimensional imaging element 65. The anterior chamber observation optical system 60 is also used as a detection optical system that detects a state of alignment of the device main body with respect to the subject's eye.

The infrared light sources 55 (in the embodiment, two infrared light sources 55 are disposed; however, the number of infrared light sources 55 is not limited to two) are disposed in the vicinity of a hole of the hole mirror 22, and are used so as to form an optical alignment index (the working dot W) on the cornea of the subject's eye. The light source 55 may be configured to guide infrared light to an optical fiber, an end surface of which is disposed in the vicinity of the hole mirror 22. When an operation distance between the subject's eye E and the photography unit (the device main body) 3 is appropriate, the cornea-reflected light produced by the light source 55 is imaged on an imaging surface of the imaging element 38. Accordingly, the inspector performs a fine adjustment of alignment using the working dot formed by the light source 55 in a state where the fundus image is displayed on a monitor 8.

<OCT Optical System>

The following description is given with reference to FIG. 2. The OCT optical system 200 is configured like a so-called optical coherence tomography (OCT)-based ophthalmic device, and captures a tomographic image of the eye E. In the OCT optical system 200, a coupler (an optical divider) 104 divides light emitted from the measurement light source 102 into measurement light (sample light) and reference light. The OCT optical system 200 guides the measurement light to the fundus Ef of the eye E, and guides the reference light to a reference optical system 110. The measurement light reaches the scanning unit 108 via a collimator lens 123 and a focus lens 124, and a reflected direction of the measurement light is changed by the driving of two galvanometer mirrors. After the measurement light reflected by the scanning unit 108 is reflected by the dichroic mirror 24, the measurement light concentrates on the fundus of the subject's eye via the objective lens 25. Thereafter, coherence light obtained by combining the measurement light reflected by the fundus Ef and the reference light is received by the detector (photodetector) 120.

The detector 120 detects a state of coherence between the measurement light and the reference light. When Fourier domain OCT is adopted, the spectral intensity of the coherence light is detected by the detector 120, and a predetermined range of a depth profile (A scan signal) is acquired by Fourier-converting spectral intensity data. For example, spectral-domain OCT (SD-OCT) or swept-source OCT (SS-OCT) may be adopted. When the spectral-domain OCT (SD-OCT) is adopted, a wide bandwidth light source is used as the light source 102, and a spectrometer is used as the detector 120. When the swept-source OCT is adopted, a variable wavelength light source is used as the light source 102, and a single photodiode is used as the detector 120 (the detection of equilibrium may be performed). In addition, time-domain OCT (TD-OCT) may be adopted.

The scanning unit 108 scans light emitted from the measurement light source on the fundus of the subject's eye. For example, the scanning unit 108 scans the measurement light on the fundus in two dimensions (in an X-Y direction (vertical direction)). The scanning unit 108 is disposed substantially conjugately with the pupil. For example, the scanning unit 108 is two galvanometer mirrors, and a reflected angle of the scanning unit 108 is arbitrarily adjusted by a drive unit 151.

Accordingly, a reflected (advance) direction of luminous flux emitted from the light source 102 is changed, and is scanned on the fundus in an arbitrary direction. Accordingly, an imaging position on the fundus Ef is changed. The scanning unit 108 may be configured to deflect light. For example, an acousto optical modulator (AOM) other than a reflective mirror (a galvanometer mirror, a polygon mirror, or a resonant scanner) may be used so as to change an advance (deflection) direction of light.

The reference optical system 110 generates the reference light to be combined with the reflected light acquired by the reflection of the measurement light from the fundus Ef. The reference optical system 110 may be Michelson type or may be Mach-Zehnder type.

The reference optical system 110 may change an optical path length difference between the measurement light and the reference light by moving an optical member on the reference optical path. For example, a reference mirror 131 moves in an optical axis direction. The configuration of changing the optical path length difference may be disposed on the measurement optical path of the measurement optical system.

More specifically, the reference optical system 110 mainly includes a collimator lens 129, the reference mirror 131, and a reference mirror drive unit 150. The reference mirror drive unit 150 is disposed on the reference optical path, and is configured such that the reference mirror drive unit 150 can move in the optical axis direction so as to change the optical path length of the reference light. The light is reflected by the reference mirror 131, and thereby the light returns to the coupler 104 again, and is guided to the detector 120. In another example, the reference optical system 110 may be a transmittance optical system (for example, an optical fiber), and light from the coupler 104 does not return, transmits through the transmittance optical system, and is guided to the detector 120.

<Control Unit>

Figure 6:
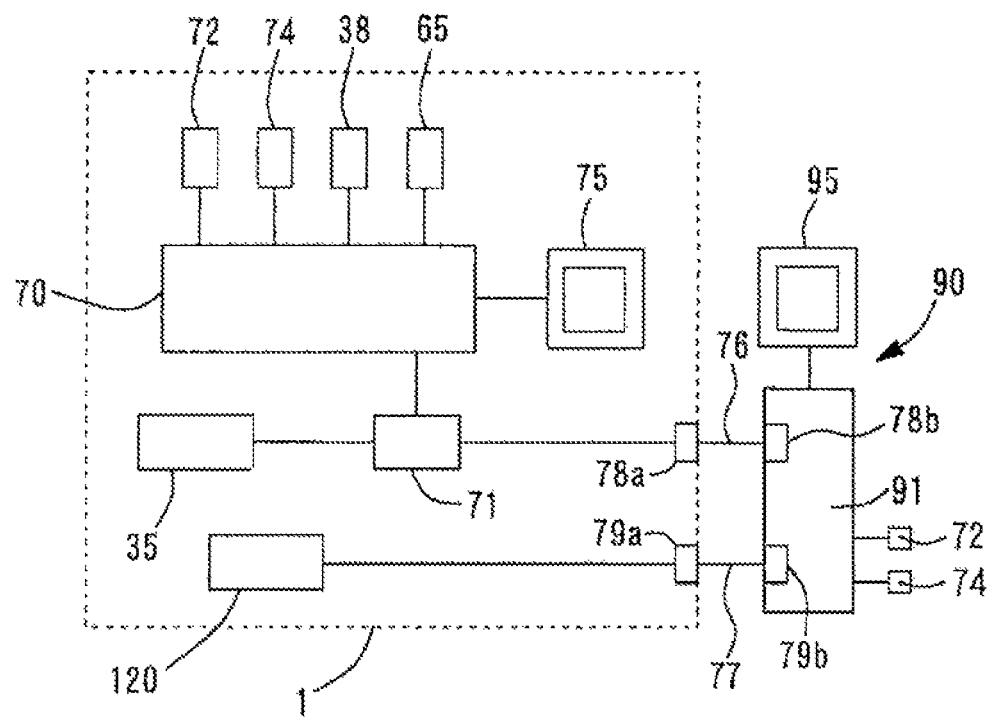
FIG. 6 is a block diagram illustrating the control system according to the embodiment.

Subsequently, a control system in this example will be described with reference to FIG. 6. As illustrated in FIG. 6, the following are connected to the control unit 70 in this example: the imaging element 65 for anterior chamber observation; the imaging element 38 for infrared fundus observation; the display unit 75; the operation unit 74; a HUB 71 compliant with USB 2.0 standards; various light sources (not illustrated); various actuators (not illustrated); and the like. The USB 2.0 compliant HUB 71 is connected to the imaging element 35 built into the device main body 1 and the personal computer (PC) 90.

The PC 90 includes a CPU 91 as a processor; an operation input unit (for example, a mouse, a keyboard); a memory (a non-volatile memory) 72 as storage means; and a display unit 95. The CPU 91 may control the device main body 1. The memory 72 is a non-transitory storage medium that can maintain stored content even when the supply of electrical power is shut off. For example, the memory 72 may be a USB memory insertably and removably mounted on a hard disc drive, a flash ROM, or the PC 90, an external server, or the like. The memory 72 stores a photography control program for controlling the device main body (ophthalmic photography device) 1 to photograph a front image and a tomographic image.

The memory 72 stores an ophthalmic analysis program that is used when the PC 90 is used as an ophthalmic analysis device. That is, the PC 90 may also be used as the ophthalmic analysis device. The memory 72 stores various pieces of information regarding photography, for example, information regarding a tomographic image (OCT data) in scanning lines, a three-dimensional tomographic image (three-dimensional OCT data), a fundus front image, and a photographic position of a tomographic image. The operation input unit receives various operation instructions from the inspector.

The detector (for example, a line CCD) 120 for OCT photography built into the device main body 1 is connected to the PC 90 through a USB signal line via USB 3.0 ports 79a and 79b. In this example, as such, the device main body 1 and the PC 90 are connected to each other through two USB signal lines 76 and 77.

The control unit 70 may detect an alignment index from an anterior chamber observation image 81 captured by the imaging element 65, and process the alignment index. The control unit 70 may detect the amount of deviation of the alignment of the device main body 1 with respect to the subject's eye based on an imaging signal from the imaging element 65.

Figure 5:
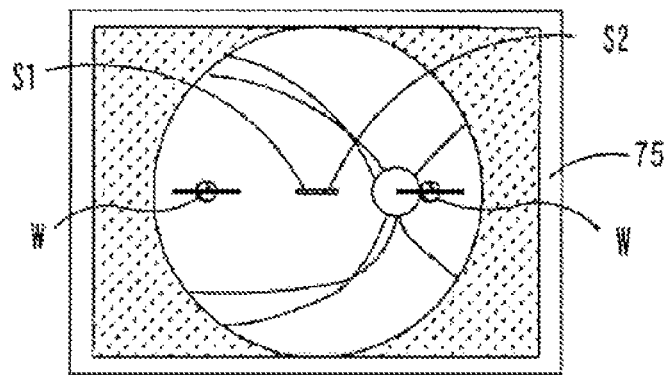
FIG. 5 illustrates an example in which a fundus image captured by the imaging element is displayed on the display unit.

The control unit 70 may electronically form and display a reticle (an alignment reference) LT at a predetermined position on a screen of the display unit 75 as illustrated on an anterior chamber image observation screen in FIG. 4 (may be illustrated on a fundus observation screen in FIG. 5). The control unit 70 may control a display of an alignment index A1 in such a manner that a relative distance between the alignment index A1 and the reticle LT is changed based on the detected amount of alignment deviation.

The control unit 70 displays the anterior chamber observation image captured by the imaging element 65, and the anterior chamber observation image and the infrared fundus observation image captured by the imaging element 38 on the display unit 75 of the main body.

The control unit 70 streamingly outputs the anterior chamber observation image and the fundus observation image to the PC 90 via the HUB 71 and the USB 2.0 ports 78a and 78b. The PC 90 displays the anterior chamber observation image and the fundus observation image 82 (which are streamingly output) on the display unit 95 of the PC 90. The anterior chamber observation image and the fundus observation image (the anterior chamber observation image 81 and the fundus observation image 82 in FIG. 3) may be simultaneously displayed as live images (for example, live front images) on the display unit 95.

The imaging element 35 photographs a color fundus image based on a trigger signal from the control unit 70. The color fundus image is also output to the control unit 70 and the PC 90 via the HUB 71 and the USB 2.0 ports 78a and 78b, and is displayed on the display unit 75 or the display unit 95 of the PC 90.

In addition, the detector 120 is connected to the PC 90 via the USB 3.0 ports 79a and 79b. A photodetection signal from the detector 120 is input to the PC 90. The PC 90 (more specifically, the processor (for example, CPU) of the PC 90) generates a tomographic image 83 by computationally processing the photodetection signal from the detector 120.

For example, when the Fourier domain OCT (for example, the spectral-domain OCT) is adopted, the PC 90 processes a spectroscopic signal containing a coherence signal of each wavelength output from the detector 120. The PC 90 obtains inside information (for example, depth data of the subject's eye (depth information)) regarding the subject's eye by processing the spectroscopic signal. More specifically, the spectroscopic signal (spectral data) is written as a function of the wavelength $\lambda$, and is converted into an equal interval function I (k) of a wavenumber k ($=2\pi/\lambda$). The PC 90 obtains a signal distribution in a depth (in the Z direction) region by Fourier-converting the spectroscopic signal in a space of the wavenumber k.

In addition, the PC 90 may obtain information (for example, a tomographic image) regarding the subject's eye along with inside information obtained at different positions by the scanning of measurement light. The PC 90 stores an obtained result in the memory 72. The PC 90 may display the obtained result on the display unit 95.

The device main body 1 performs photography according to a pre-set scanning pattern based on a release signal from the PC 90. The PC 90 processes photographic signals, and outputs an imaging result on the display unit 95 of the PC 90.

At this time, the detector 120 outputs detection signals to the PC 90. The PC 90 generates a tomographic image from the detection signals from the detector 120.

The PC 90 transmits the generated tomographic image to the device main body 1 via the USB 2.0 ports 78a and 78b and the HUB 71. The control unit 70 displays the transmitted tomographic image 83 on the display unit 75 (for example, refer to the tomographic image 83). The PC 90 may generate an OCT front image from the output signals from the detector 120, and display the OCT front image on the display unit 75 or the display unit 95.

Figure 1B:
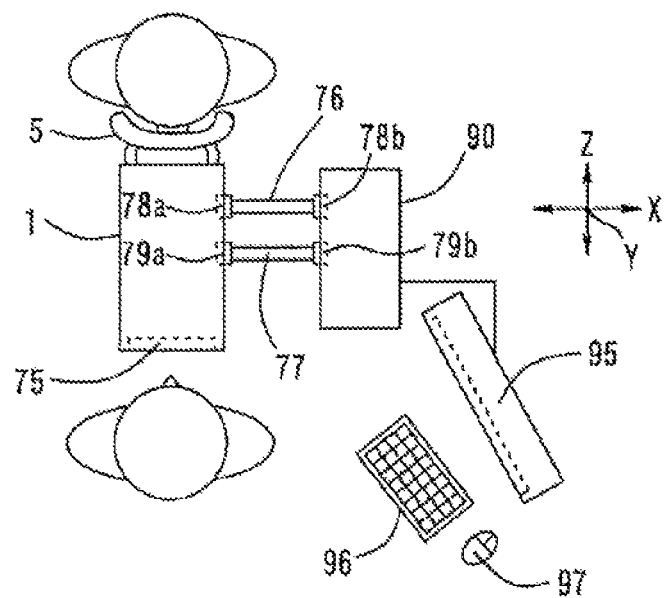

In this example, the inspector can perform set operations such as a setting for OCT photography, alignment, or optimization, or perform a positional alignment, while watching the display unit 75 provided in the device main body 1 (details will be described later). Accordingly, as illustrated in FIG. 1(b), the inspector is not required to put effort into alternately confirming the display unit 75 of the device main body 1 and the display unit 95 of the PC 90 which are disposed at different positions. In addition, when the inspector opens an eyelid and performs photography, it may be easier for the inspector to open the eyelid while confirming the display unit 75 than opening the eyelid while confirming the display unit 95 of the PC 90.

In addition, since the tomographic image 83, the fundus image 82, the anterior chamber observation image 81, and the like are displayed on both the display unit 75 and the display unit 95 of the PC 90, the inspector can preferably select between an operation via the device main body 1 and an operation via the PC 90. Since various photographed images are displayed on both the display unit 75 and the display unit 95 of the PC 90, it is possible to increase the number of screens on which images can be observed, and two or more persons can easily confirm the images.

When one inspector observes images on the display unit 95 of the PC 90, and the other inspector performs photography using the device main body 1, that is, two inspectors separately perform a measurement, the inspector who performs photography can confirm the photographed tomographic image 83 on the display unit 75, and can redo the photography when the photography cannot be well performed. For this reason, it is less frequent for the inspector who observes the display unit 95 to notify the inspector who performs photography that the redoing of a measurement is required.

In this manner, since the tomgoraphic image 83 is displayed on both the display unit 75 of the device main body 1 and the display unit 95 of the PC 90, the device main body 1 is adaptable to a preferred photography method of the inspector.

Similarly, this also applies to the color fundus photography. It may be possible to not only input a color fundus photography result to the PC 90, but also to transmit image information such as a preview result to the device main body 1 via the USB 2.0 ports 78a and 78b and the HUB 71, and to display a color fundus image on the display unit 75 of the device main body 1. Accordingly, the inspector is not required to put effort in alternately confirming the device main body 1 and the PC 90 so as to watch the color fundus image. In a case where the inspector operates the device main body 1 while watching the color fundus photography image, since the inspector is required to confirm only the display unit 75 without glancing the display unit 95 of the PC 90, the inspector has less burden.

<Control Operation>

Figure 3A:
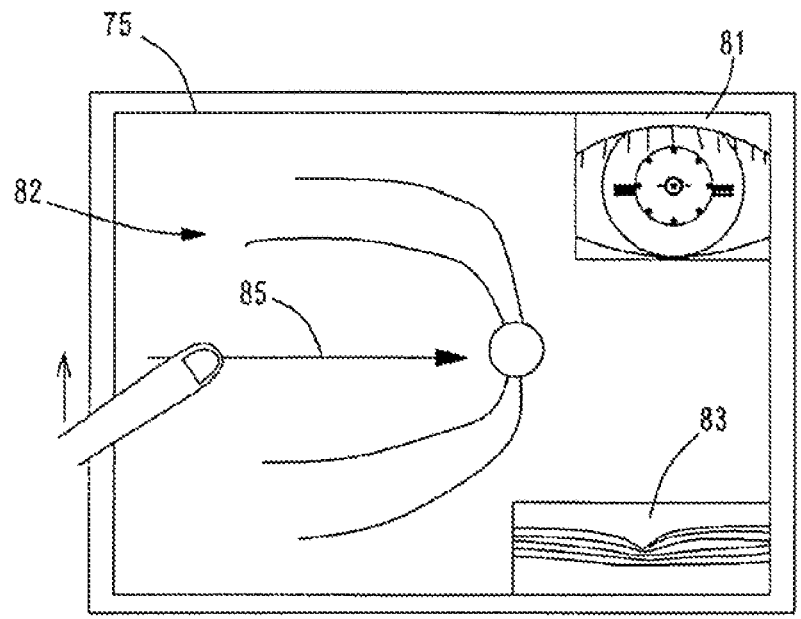
FIGS. 3A and 3B show views illustrating an example of a screen displayed on a display unit according to the embodiment.
Figure 3B:
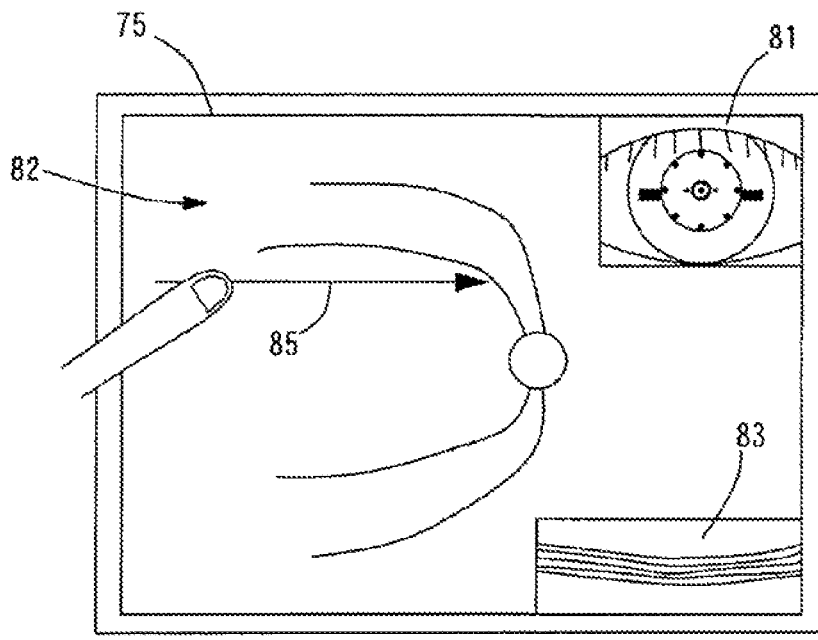

An example of a control operation of the device having the above-mentioned configuration will be described hereinbelow. For example, the control unit 70 may combine an image captured by the imaging element 65, an image captured by the imaging element 38, and an OCT image from the PC 90, and display the combined image on an observation screen on the display unit 75. As illustrated in FIG. 3, the observation screen may simultaneously display the anterior chamber observation image 81, the fundus observation image 82, and the tomographic image in a live mode.

The tomographic image 83 is output from the PC 90 to the control unit 70 from via the USB 2.0 ports 78a and 78b, and is displayed on the display unit 75. In this embodiment, the display unit 75 displays the fundus image 82, the anterior chamber observation image 81, and the tomographic image 83 on a center portion, an upper right portion, and a lower right portion of the display unit 75, respectively; however, the image display positions are not limited to those in this embodiment. The inspector operates the device main body 1 while confirming the images on the display unit 75.

The inspector gets the subject's face supported by the face support unit 5. The inspector instructs the subject to watch a fixed visual target (not illustrated). In an initial stage, the dichroic mirror 24 is inserted on the optical path of the photography optical system 30, and the display unit 75 displays the anterior chamber image captured by the imaging element 65.

The inspector moves the photography unit 3 in the vertical and lateral directions by adjusting alignment in the vertical and lateral directions, for example, by operating the joystick 74a, in such a manner that the anterior chamber image appears on the display unit 75. As illustrated in FIG. 4, when the alignment is adjusted in order for the anterior chamber image to appear on the display unit 75, eight index images (first alignment index images) Ma to Mh appear. At this time, the imaging range of the imaging element 65 preferably includes the pupil of the anterior chamber, an iris, and an eyelash when the alignment is completed.

<Alignment Detection and Automatic Alignment in X, Y, and Z Directions>

When the alignment index images Ma to Mh are detected by the two-dimensional imaging element 65, the control unit 70 starts automatic alignment control. The control unit 70 detects the amount Δd of deviation of the alignment of the photography unit 3 with respect to the subject's eye based on an imaging signal from the two-dimensional imaging element 65. More specifically, an X-Y coordinate of the center of a ring shape formed by the index images Ma to Mh projected in a ring shape is detected as a substantially center of the cornea, and the amount Δd of deviation between a pre-set alignment reference position O1 (for example, the intersection of an imaging surface of the imaging element 65 and the photography optical axis L1) on the imaging element 65 in the X and Y directions, and the center coordinate of the cornea is obtained (refer to FIG. 7). The center of the pupil may be detected by processing images, and an alignment deviation may be detected based on the amount of deviation between the coordinate position and the reference position O1.

The control unit 70 controls the driving of the XYZ drive unit 6 to perform automatic alignment in such a manner that the amount Δd of deviation is present in an alignment completion allowable range A. The suitability of the alignment in the X and Y directions is determined based on whether the amount Δd of deviation is continuously present in the alignment completion allowable range A for a constant amount of time (for example, for 10 frames of the image processing or 0.3 seconds) (whether an alignment condition A is satisfied).

In addition, the control unit 70 obtains the amount of alignment deviation in the Z direction by comparing the distance between the infinite index images Ma and Me and the distance between the finite index images Mh and Mf detected as described above. At this time, the control unit 70 obtains the amount of alignment deviation with the subject's eye in a direction of the operation distance based on characteristics by which when the photography unit 3 deviates in the direction of the operation distance, the distance between the infinite index images Ma and Me is not nearly changed, and the distance between the index images Mh and Mf is changed (specifically, refer to JP-A-6-46999).

The control unit 70 also obtains the amount of deviation in the Z direction with respect to an alignment reference position, and controls the driving of the XYZ drive unit 6 to perform automatic alignment in such a manner that the amount of deviation is present in an alignment completion allowable range. The suitability of the alignment in the Z direction is determined based on whether the amount of deviation in the Z direction is present in the alignment completion allowable range for a constant amount of time (whether an alignment condition is satisfied).

When the alignment in the X, Y, and Z directions satisfies the alignment completion condition via the alignment operation, the control unit 70 determines that the alignment in the X, Y, and Z directions is met, and proceeds to the next step.

Here, when the amount Δd of alignment deviation in the X, Y, and Z directions is present in an allowable range A1, the control unit 70 stops the driving of the drive unit 6, and outputs an alignment completion signal. Even after the alignment is completed, the control unit 70 frequently detects the amount Δd of deviation, and when the amount Δd of deviation exceeds the allowable range A1, the control unit 70 restarts automatic alignment. That is, the control unit 70 controls the photography unit 3 to track the subject's eye in such a manner that the amount Δd of deviation is present in the allowable range A1.

<Determination of Diameter of Pupil>

After the alignment is completed, the control unit 70 starts a process of determining whether the pupil of the subject's eye is in a suitable state. At this time, the suitability of a pupil diameter is determined based on whether a pupil edge from the anterior chamber image detected by the imaging element 65 is out of a predetermined pupil determination area. The pupil determination area is set to have the size of a diameter (for example, a diameter of 4 mm) around an image center (photography optical axis center), through which the fundus illumination luminous flux can pass. In a simple manner, four pupil edges detected laterally and vertically with respect to the image center are used. When the pupil edge points are out of the pupil determination area, the amount of illumination light for photography is sufficiently ensured (specifically, refer to JP-A-2005-160549 filed by the applicant). The suitability of the pupil diameter is continuously determined until the photography is performed, a determination result is displayed on the display unit 75.

<Detection of State of Focus and Autofocus>

When the alignment is completed using the imaging element 65, the control unit 70 performs an autofocus on the fundus of the subject's eye. FIG. 5 illustrates an example of a fundus image captured by the imaging element 38, and the focus index images S1 and S1 are projected to the center of the fundus image by the focus index projection optical system 40. Here, when the focus index images S1 and S2 are not in focus, the focus index images S1 and S2 are projected while being separated from each other, and when the focus index images S1 and S2 are in focus, the focus index images S1 and S2 are projected while matching each other. The control unit 70 detects the index images S1 and S2 by processing the images, and obtain information regarding the separation of the images. The control unit 70 controls the driving of the moving mechanism 49 based on the information regarding the separation of the index images S1 and S2, and moves the lens 32 so as to focus on the fundus.

<Optimization Control>

When an alignment completion signal is output, the control unit 70 generates a trigger signal for starting optimization control, and starts an optimization control operation. When the control unit 70 performs the optimization control, the inspector can observe a desired fundus portion at high sensitivity and high resolution. In this embodiment, the optimization control is the controlling of an optical path length adjustment, a focus adjustment, and a polarization state adjustment (polarizer adjustment). In the optimization control, constant allowable conditions relative to the fundus can be preferably satisfied, and the best optimized state is not necessarily obtained via the optimization control.

In an initialization control of the optimization control, the control unit 70 sets the positions of the reference mirror 131 and the focusing lens 124 to initial positions, respectively. After the initialization control is completed, the control unit 70 performs a first optical path length adjustment (a first automatic optical path adjustment) by moving the reference mirror 131 from the set initial position by predetermined steps in one direction. In parallel with the first optical path length adjustment, the control unit 70 acquires focal position information (for example, the amount of movement of the lens 32) based on a result of a focus on the fundus of the subject's eye performed by the fundus camera optical system. When the focal position information is acquired, the control unit 70 performs an autofocus adjustment (focus adjustment) by moving the focusing lens 124 to a focal position. The focal position is preferably a position in which it is possible to acquire an allowable contrast of a tomographic image as an observation image, and the focal position is not necessarily an optimized focal position.

After the focus adjustment is completed, the control unit 70 performs a second optical path length adjustment in which an optical path length is re-adjusted (an optical path length is finely adjusted) by moving the reference mirror 131 in the optical axis direction again. After the second optical path length adjustment is completed, the control unit 70 adjusts a polarization state of measurement light by driving a polarizer 133 for adjusting a polarization state of reference light (specifically, refer to JP-A-2012-56292).

As such, when the optimization control is completed, the inspector can observe a desired fundus portion at high sensitivity and high resolution. The control unit 70 controls the driving of the scanning unit 108 to scan measurement light on the fundus.

A detection signal (spectral data) from the detector 120 is transmitted to the PC 90 via the USB 3.0 ports 79a and 79b (refer to FIG. 6). The PC 90 receives the detection signal, and generates a tomographic image 83 by computationally processing the detection signal.

When the PC 90 generates the tomographic image 83, the PC 90 transmits the tomographic image 83 to the control unit 70 of the device main body 1 via the USB 2.0 ports 78a and 78b and the HUB 71. The control unit 70 receives the tomographic image 83 from the PC 90 via the USB 2.0 ports 78a and 78b and the HUB 71, and displays the tomographic image 83 on the display unit 75. As illustrated in FIG. 3, the control unit 70 displays the anterior chamber observation image 81, the fundus observation image 82, and the tomographic image 83 on the display unit 75.

The inspector confirms the tomographic image 83 which is being updated real-time, and adjusts an alignment in the Z direction. For example, the alignment may be adjusted in such a manner that the tomographic image 83 is fitted in a display frame.

Naturally, the PC 90 may display the generated tomographic image 83 on the display unit 95. The PC 90 may display the generated tomographic image 83 on the display unit 95 real-time. In addition to the tomographic image 83, the PC 90 may display the anterior chamber observation image 81 and the fundus observation image 82 on the display unit 95.

In the description, the inspector manually adjusts an image focus by operating an adjustment knob 74d or the like; however, the present invention is not limited to the method given in this embodiment. For example, the inspector may adjust an image by touching the display unit (for example, the display unit 75) having a touch panel function.

When the alignment and the image quality adjustment are completed, the control unit 70 forms an tomographic image by controlling the driving of the scanning unit 108 to scan measurement light on the fundus in a predetermined direction, and acquiring a photodetection signal corresponding to a predetermined scan region from an output signal from the detector 120 during the scanning operation.

FIG. 3 shows views illustrating an example of a display screen displayed on the display unit 75. The control unit 70 displays the anterior chamber observation image 81 acquired by the anterior chamber observation optical system 60, the fundus observation image 82, and the tomographic image 83, and a line 85 on the display unit 75. The line 85 is an index indicative of a measurement position (an acquisition position) for a tomographic image on the fundus observation image 82. The line 85 is electrically displayed on the fundus observation image 82 on the display unit 75.

In the configuration of this example, the inspector can set photographic conditions by performing a touch operation or a drag operation on the display unit 75. The inspector can specify an arbitrary position on the display unit 75 via a touch operation.

<Setting of Scanning Lines>

FIG. 3 shows views illustrating the setting of a scanning position. When the tomographic image and the fundus observation image 82 are displayed on the display unit 75, the inspector set a position of a tomographic image to be photographed on the fundus observation image 82 being observed real-time on the display unit 75. Here, the inspector moves the line 85 with respect to the fundus observation image 82 and sets a scanning position by performing a drag operation via the touch panel display unit 75. When the line is set in the X direction, a tomographic image in an X-Z plane is photographed, and when the line 85 is set in the Y direction, a tomographic image in an Y-Z plane is photographed. It may be possible to set the shape of the line 85 to an arbitrary shape (for example, a diagonal line or a circular line).

In this example, the operation of the touch panel display unit 75 provided in the device main body 1 has been described; however, the present invention is not limited to the operation method given in this example. Similar to the display unit 75, it may be possible to operate the joystick 74a or various operation buttons provided in the operation unit 74 of the device main body 1. At this time, for example, an operation signal from the operation unit 74 may be transmitted to the PC via the control unit 70, and the PC may transmit a control signal to the control unit 70 in response to the operation signal.

When the inspector moves the line 85 with respect to the fundus observation image 82, the control unit 70 frequently sets a scanning position, and acquires the corresponding tomographic image at the scanning position. The acquired tomographic image is frequently on a display screen on the display unit 75. The control unit 70 changes a scanning position of the measurement light based on an operation signal from the display unit 75, and displays the line 85 at a display position corresponding to the changed scanning position. Since a relationship between the display position (a coordinate position on the display unit) of the line 85 and the scanning position of the measurement light by the scanning unit 108 is determined in advance, the control unit 70 properly controls the driving of the two galvanometer mirrors of the scanning unit 108 in such a manner that the measurement light is scanned in a scanning range corresponding to the display position of the line 85 which is set.

<Acquisition of Tomographic Image>

After the setting of the photography conditions is completed, and when the inspector operates a photography start switch 74c to a desired position, the control unit 70 acquires a tomographic image by performing B scan based on the set scanning position. The control unit 70 drives the scanning unit 108 to scan measurement light in such a manner that a tomographic fundus image corresponding to the position of the line 85 is obtained based on the display position of the line 85 set on the fundus observation image 82.

The PC 90 generates a still tomographic image based on a detection signal from the detector 120, and transmits the generated still image to the device main body 1. The control unit 70 controls the display unit 75 to display the still tomographic image transmitted from the PC 90.

For example, the control unit 70 may display an OK button and a cancel button (not illustrated) on the display unit 75. The inspector presses the OK button when the inspector desires to retain the tomographic image 83 displayed on the display unit 75 in the memory 72, and presses the cancel button when the inspector does not desire to retain the tomographic image 83. When the OK button is pressed, the control unit 70 stores the tomographic image 83 in the memory 72. In contrast, when the cancel button is pressed, the control unit 70 may redo the photography of the tomographic image 83.

As such, since the tomographic image 83 is displayed on the display unit 75, the inspector can determine whether the photography is properly performed without the aid of the PC 90.

When the tomographic image is obtained, the control unit 70 proceeds to a step in which the color fundus image 82 is acquired by the fundus camera optical system 100. The inspector performs a fine adjustment of the alignment and the focus so as to obtain a desired state of images while observing the fundus observation image 82 displayed on the display unit 75. When the inspector turns on the photography start switch 74c, the photography is performed. The control unit 70 retracts the dichroic mirror 24 out of the optical path by driving the insertion and removal mechanism 66 based on a trigger signal via the photography start switch 74c, and controls the photography light source 14 to emit light.

The fundus of the subject's eye is illuminated by visible light emitted from the photography light source 14. The reflected light from the fundus passes through the objective lens 25, the opening of the hole mirror 22, the photographic diaphragm 31, the focusing lens 32, the imaging lens 33, and the dichroic mirror 37, and is imaged on the two-dimensional photodetector 35. The color fundus image photographed by the two-dimensional photodetector 35 is received by the PC 90 via the HUB 71 and the USB 2.0 ports 78a and 78b, and thereafter, the color fundus image is stored in the memory 72.

The PC 90 performs a process of analyzing at least either one of the acquired tomographic image and the fundus image, and display an analysis result on the display unit 95. The PC 90 may display the analysis result on the display unit 75.

DESCRIPTION OF REFERENCE NUMERALS AND SIGNS

1: device main body
10: fundus illumination optical system
22: hole mirror
24: dichroic mirror
25: objective lens
30: fundus photography optical system
58: anterior chamber illumination light source
60: anterior chamber observation optical system
61: dichroic mirror
70: control unit
75: display unit
90: computer
95: display unit
102: measurement light source
200: coherence optical system (OCT optical system)
EX: exciter filter
BA: barrier filter

What is claimed is:

1. A fundus photography device comprising:
a fundus illumination optical system including at least a photography light source and an observation light source, the fundus illumination optical system configured to illuminate a fundus of a subject's eye;
a fundus photography optical system including at least a first imaging sensor configured to photograph the fundus, and a second imaging sensor configured to observe the fundus, the fundus photography optical system configured to photograph a front image of the fundus;
an OCT optical system including at least a measuring light path, a reference light path, and a photodetector configured to detect an interference signal between light from the measuring light path and light from the reference path, and configured to obtain a tomographic image of the fundus using optical coherence tomography;
an objective lens configured to be disposed in front of the subject's eye;
a hole mirror;
an anterior eye observation optical system configured to observe an anterior eye of the subject's eye;
a first wavelength selective splitter disposed between the objective lens and the hole mirror, and configured to set a first optical axis commonly shared by the fundus illumination optical system and the fundus photography optical system to be coaxial with a second optical axis commonly shared by the OCT optical system and the anterior eye observation optical system; and
a second wavelength selective splitter disposed upstream of the second wavelength selective splitter, and configured to set an optical axis of the OCT optical system to be coaxial with an optical axis of the anterior chamber observation optical system to form the second optical axis.

2. The fundus photography device according to claim 1, wherein
the OCT optical system comprises an OCT light source configured to emit light having a center wavelength between 800 nm and 900 nm,
the anterior eye observation optical system comprises a light source configured to emit light having a center wavelength between 900 nm and 1000 nm,
the observation light source is configured to emit light having a center wavelength between 750 nm and 800 nm, and the photography light source is configured to emit visible bandwidth light having a wavelength less than 750 nm, and
the first wavelength selective splitter has a cut-on wavelength between 760 nm and 840 nm, and has wavelength characteristics so as to transmit at least light having a wavelength corresponding to the light from the observation light source, and to reflect light having a wavelength corresponding to the light from the OCT light source and light having a wavelength corresponding to a reflected light produced by the light source of the anterior eye observation optical system.

3. The fundus photography device according to claim 1, wherein
the OCT optical system comprises an OCT light source configured to emit light having a center wavelength between 1000 nm and 1350 nm,
the anterior eye observation optical system comprises a light source configured to emit light having a center wavelength between 900 nm and 1000 nm,
the observation light source is configured to emit light having a center wavelength between 750 nm and 900 nm, and the photography light source is configured to emit visible bandwidth light having a wavelength less than 750 nm, and
the first wavelength selective splitter has a cut-on wavelength between 760 nm and 900 nm, and has wavelength characteristics so as to transmit at least light having the wavelength corresponding to light from the observation light source, and light having the wavelength corresponding to the light from the OCT light source and a reflected light produced by the light source of the anterior eye observation optical system.

4. The fundus photography device according to claim 1, wherein the anterior eye observation optical system includes a cut filter disposed on an optical path on a downstream side of the second wavelength selective splitter, the cut filter is configured to cut off light having a wavelength bandwidth corresponding to the light from the OCT light source.

* * * * *